United States Patent
Sun et al.

(10) Patent No.: US 12,386,005 B2
(45) Date of Patent: Aug. 12, 2025

(54) PHANTOM FOR MULTINUCLEAR SIMULTANEOUS INTEGRATED MAGNETIC RESONANCE IMAGING AND APPLICATION METHOD THEREOF

(71) Applicant: Harbin Medical University, Harbin (CN)

(72) Inventors: Xilin Sun, Harbin (CN); Chunsheng Yang, Harbin (CN); Kai Wang, Harbin (CN); Pengcheng Cheng, Harbin (CN); Lijiao Wang, Harbin (CN); Lili Yang, Harbin (CN); Yongyi Wu, Harbin (CN); Lina Wu, Harbin (CN)

(73) Assignee: HARBIN MEDICAL UNIVERSITY, Harbin (CN)

( * ) Notice: Subject to any disclaimer, the term of this patent is extended or adjusted under 35 U.S.C. 154(b) by 0 days.

(21) Appl. No.: 19/006,271

(22) Filed: Dec. 31, 2024

(65) Prior Publication Data
US 2025/0180686 A1  Jun. 5, 2025

Related U.S. Application Data

(63) Continuation of application No. PCT/CN2024/082841, filed on Mar. 21, 2024.

(30) Foreign Application Priority Data

Apr. 4, 2023 (CN) .................. 202310349168.2

(51) Int. Cl.
*G01R 33/58* (2006.01)
*A61B 5/055* (2006.01)
*G01R 33/36* (2006.01)

(52) U.S. Cl.
CPC .......... *G01R 33/58* (2013.01); *G01R 33/3635* (2013.01); *A61B 5/055* (2013.01)

(58) Field of Classification Search
CPC .............. G01R 33/3635; G01R 33/58; G01R 33/4828; A61B 5/0228; A61B 5/055
See application file for complete search history.

(56) References Cited

U.S. PATENT DOCUMENTS

| 8,814,572 B2 * | 8/2014 | Eberler | G01R 33/58 434/267 |
| 9,603,546 B2 * | 3/2017 | Horkay | G01R 33/56341 |

(Continued)

FOREIGN PATENT DOCUMENTS

| CN | 102023288 A | * | 4/2011 |
| CN | 203244393 U | | 10/2013 |

(Continued)

OTHER PUBLICATIONS

Translation CN 102023288 (Year: 2011).*

(Continued)

*Primary Examiner* — Steven L Yeninas
(74) *Attorney, Agent, or Firm* — Bayramoglu Law Offices LLC

(57) ABSTRACT

A phantom for multinuclear simultaneous integrated magnetic resonance imaging includes a plurality of sealed containers, where a partition I and a partition II are provided in the sealed container and intersect with each other; the partition I and the partition II divide the sealed container into a plurality of subspaces that are interconnected; a thickness of the partition I is equal to a resolution of a nuclide $^1$H, and a thickness of the partition II is $\gamma_H/\gamma_X$ times of the resolution of the nuclide $^1$H, where $\gamma_H$ is a gyromagnetic ratio of the nuclide $^1$H, and $\gamma_X$ is a gyromagnetic ratio of a pre-imaging nuclide X; the sealed container is filled with a mixture; and the mixture includes all pre-imaging nuclides. In the phantom, the partition I and the partition II are designed accord- (Continued)

ing to a ratio of gyromagnetic ratios of nuclides, and are combined with a mixture including all pre-imaging nuclides.

20 Claims, 3 Drawing Sheets

(56) References Cited

U.S. PATENT DOCUMENTS

| | | |
|---|---|---|
| 2004/0032977 A1 | 2/2004 | Blezek et al. |
| 2008/0265882 A1 | 10/2008 | Wiggins |
| 2008/0297151 A1* | 12/2008 | Hirata .................... G01R 33/58 324/307 |
| 2009/0118611 A1* | 5/2009 | He ........................ G01R 33/341 324/322 |
| 2013/0096415 A1 | 4/2013 | Ruff et al. |
| 2015/0077104 A1* | 3/2015 | Diehl .................... G01N 24/087 324/307 |
| 2015/0323639 A1 | 11/2015 | Boss |
| 2020/0330619 A1 | 10/2020 | Swanson et al. |
| 2023/0366967 A1* | 11/2023 | Swanson ............ G01R 33/5605 |
| 2024/0272253 A1* | 8/2024 | Ham .................... G01R 33/302 |

FOREIGN PATENT DOCUMENTS

| | | | |
|---|---|---|---|
| CN | 204995476 U | | 1/2016 |
| CN | 105342614 A | | 2/2016 |
| CN | 110811621 A | | 2/2020 |
| CN | 210514600 U | * | 5/2020 |
| CN | 112263237 A | | 1/2021 |
| CN | 113311372 A | | 8/2021 |
| CN | 113936008 A | | 1/2022 |
| CN | 114062990 A | | 2/2022 |
| CN | 116098605 A | | 5/2023 |

OTHER PUBLICATIONS

Translation CN 210514600 (Year: 2020).*
CN 210514600 and Machine Translation (Year: 2020).*
Wang Rong, et al., The value of self-made water phantom for 3.0T MRI cervical fat-suppression sequence scan, J Chin Clin Med Imaging, 2017, pp. 166-168, vol. 28 No.3.
Zhang Jian, et al., Development of Dedicated fMRI Phantom, China Medical Equipment, 2013, pp. 27-28, 69, vol. 28 No. 11.

* cited by examiner

PHANTOM FOR MULTINUCLEAR SIMULTANEOUS INTEGRATED MAGNETIC RESONANCE IMAGING AND APPLICATION METHOD THEREOF

CROSS-REFERENCE TO THE RELATED APPLICATIONS

This application is the continuation application of International Application No. PCT/CN2024/082841, filed on Mar. 21, 2024, which is based upon and claims priority to Chinese Patent Application No. 202310349168.2, filed on Apr. 4, 2023, the entire contents of which are incorporated herein by reference.

TECHNICAL FIELD

The present disclosure relates to the technical field of magnetic resonance imaging (MRI), and in particular to a phantom and its application method for multinuclear simultaneous integrated magnetic resonance imaging.

BACKGROUND

Magnetic resonance imaging (MRI) can achieve multi-nuclear, multi-sequence, multi-parameter and multi-orientation imaging to obtain images with excellent soft tissue contrast and spatial resolution. After more than 40 years of development, MRI has played an important role in preclinical research and clinical diagnosis and treatment. Traditional MRI focuses on hydrogen ($^1H$) imaging, but in reality, all nuclides with non-zero spin quantum number, such as sodium ($^{23}Na$), fluorine ($^{19}F$), phosphorus ($^{31}P$), and chlorine ($^{35}Cl$), can be used for MRI. The imaging of endogenous nuclides such as $^{23}Na$, $^{31}P$, and $^{35}Cl$ in living organisms can provide lots of functional information like metabolism and cell activity that $^1H$ imaging can not provide. Meanwhile, exogenous nuclides have no background signal in vivo and thus can be used as targeting reagents, tracers, drug carriers, etc. for in vivo studies. For example, fluorine ($^{19}F$) can be applied to molecular imaging probes.

The functional images like physiological features provided by non-$^1H$ nuclides must be fused with $^1H$-based anatomical images to complement various types of medical information, thereby exploring molecular events in the development process of diseases and greatly improving the accuracy of disease diagnosis, staging, and efficacy evaluation. However, the fusion accuracy of multinuclear MR images is affected by various factors, mainly including the following: (1) different nuclides have different gyromagnetic ratios, which leads to significant differences in the image resolution of different nuclides; (2) different nuclides have significant differences of the gyromagnetic ratios, and the non-uniformity of the static magnetic field has different effects on the image resolution of different nuclides; and (3) non-$^1H$ nuclides have low concentrations and discontinuous distributions in living organisms, making it hard to acquire anatomical structure information and extract feature points similar to $^1H$ images from non-$^1H$ nuclide images.

Existing literature CN113311372A discloses a phantom and a testing method for an imaging uniform region of an MRI device using the phantom. In the disclosure, a grating is provided inside a shell, and is parallel or perpendicular to a magnetic pole surface of the MRI device. The imaging uniform region can be calculated without the need for a uniform field. Alternatively, the imaging uniform region of the MRI device can be acquired without a Tesla meter.

Existing literature CN210514600U discloses a dynamic phantom for quality monitoring of functional magnetic resonance imaging (fMRI). A rotating partition divides the internal space of a shell into a plurality of regions. During the simulation of fMRI, different signal states are displayed to measure the ability of signal change detection required for fMRI.

The phantoms disclosed in the above literature are aimed at $^1H$ imaging alone, and cannot achieve simultaneous integrated imaging of a plurality of nuclides or provide feature information related to differences in the gyromagnetic ratios of nuclides for the fusion of multinuclear MR images.

SUMMARY

The present disclosure proposes a phantom and its application method for multinuclear simultaneous integrated magnetic resonance imaging. In the present disclosure, a partition I and a partition II are designed according to a ratio of gyromagnetic ratios of nuclides, and are combined with a mixture including all pre-imaging nuclides. This facilitates the extraction of feature information corresponding to the resolution of nuclide images, further improving the accuracy of multinuclear image fusion.

The present disclosure is implemented by the following technical solutions. A phantom for multinuclear simultaneous integrated MRI includes a plurality of sealed containers, wherein a partition I and a partition II are provided in the sealed container and intersect with each other; the partition I and the partition II divide the sealed container into a plurality of subspaces, wherein the plurality of subspaces are interconnected; a thickness of the partition I is equal to a resolution of a nuclide $^1H$, and a thickness of the partition II is $\gamma_H/\gamma_X$ times of the resolution of the nuclide $^1H$, where X is a pre-imaging nuclide, $\gamma_H$ is a gyromagnetic ratio of the nuclide $^1H$, and $\gamma_X$ is a gyromagnetic ratio of a pre-imaging nuclide X; the sealed container is filled with a mixture; and the mixture includes all pre-imaging nuclides.

Furthermore, there are a total of n pre-imaging nuclides, where n is an integer, and n≥2; and one of the nuclides is $^1H$, while remaining nuclides are non-proton nuclides $X_1$, $X_2$, ..., and $X_{n-1}$.

Furthermore, when n=2, a remaining nuclide is a non-proton nuclide $X_1$; there are three sealed containers in total, and $\gamma_X$ of the three sealed containers is gyromagnetic ratios of $^1H$, $X_1$, and $X_1$, respectively; and the thicknesses of the partitions II of the three sealed containers are 1 time, $\gamma_H/\gamma_{X_1}$ times, and $\gamma_H/\gamma_{X_1}$ times the resolution of the $^1H$ nuclide.

Furthermore, when n≥3, remaining nuclides are non-proton nuclides $X_1$, $X_2$, ..., and $X_{n-1}$; there are n sealed containers in total, and $\gamma_X$ of the n sealed containers is gyromagnetic ratios of $^1H$, $X_1$, $X_2$, ..., and $X_{n-1}$, respectively; and the thicknesses of the partitions II of the n sealed containers are 1 time, $\gamma_H/\gamma_{X_1}$ times, $\gamma_H/\gamma_{X_2}$ times, ..., and $\gamma_H/\gamma_{X_{n-1}}$ times the resolution of the $^1H$ nuclide.

Furthermore, a resonant frequency of the pre-imaging nuclide in the mixture is consistent with an excitation frequency of the pre-imaging nuclide in a living organism.

Furthermore, MR peaks of all the nuclides in the mixture are single peaks; and alternatively, a compound where the nuclide is located belongs to a same substance as an exogenous compound injected into a living organism. For example, for imaging with a plurality of compounds including $^{31}P$ in the living organism, the mixture includes singlepeaked phosphate or phosphoric acid; and for imaging with an exogenous $^{19}$F probe, the mixture includes the exogenous $^{19}$F probe.

Furthermore, each nuclide in the mixture has a concentration greater, for example 15-25% greater than a concentration of the corresponding nuclide in the living organism.

Furthermore, the sealed container is provided with a cylindrical shell; the partition I and the partition II intersect to form a cross-shaped assembly; and an upper end and a lower end of the cross-shaped assembly are spaced apart from the sealed container to ensure that four subspaces are interconnected.

An application method of the phantom for multinuclear simultaneous integrated MRI includes: placing the plurality of sealed containers in a coplanar and non-collinear manner around a pre-imaging part, ensuring that a selected imaging slice includes central regions of the sealed containers and the partition I and the partition II that intersect are present.

Furthermore, the plurality of sealed containers are placed at equal distances around the pre-imaging part and secured with an elastic strap.

The present disclosure has the following beneficial effects:
1. The present disclosure proposes a phantom for multinuclear simultaneous integrated MRI. The present disclosure simultaneously acquires MR signals of different nuclides in the phantom and the living organism, providing feature points and structural similarity features for multinuclear MR image fusion, and laying the foundation for multinuclear image fusion.
2. In the present disclosure, the partition I and the partition II of the phantom are designed according to a ratio of gyromagnetic ratios of nuclides, and are combined with a mixture including all pre-imaging nuclides. This facilitates the extraction of feature information corresponding to the resolution of nuclide images, further improving the accuracy of multinuclear image fusion.

BRIEF DESCRIPTION OF THE DRAWINGS

To describe the technical solutions in the embodiments of the present disclosure or in the prior art more clearly, the following briefly describes the accompanying drawings required for describing the embodiments or the prior art. Apparently, the accompanying drawings in the following description show merely some embodiments of the present disclosure, and a person of ordinary skill in the art may still derive other drawings from these accompanying drawings without creative efforts.

Figure 1:
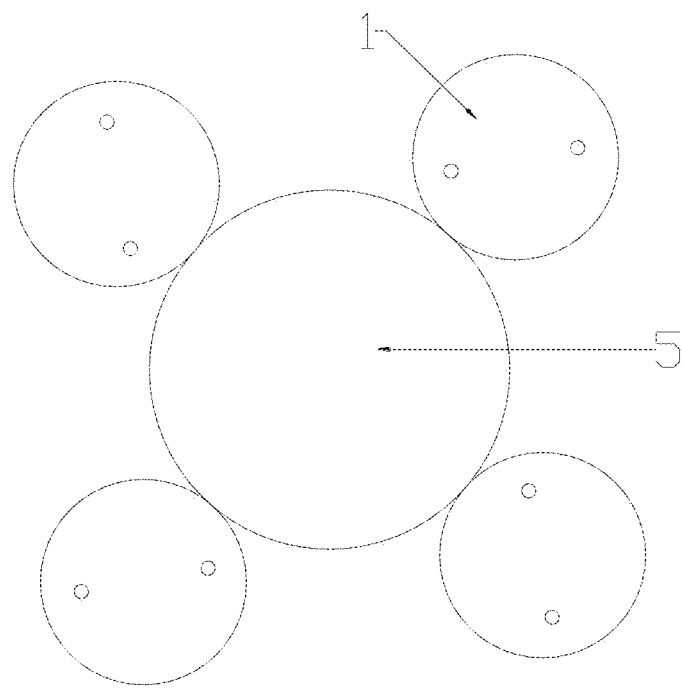
FIG. 1 is a structural diagram of a phantom.

Reference Numerals: 1. sealed container; 2. water inlet; 3. partition I; 4. partition II; and 5. pre-imaging part.

DETAILED DESCRIPTION OF THE EMBODIMENTS

The technical solutions of the embodiments of the present disclosure are clearly and completely described below with reference to the drawings in the embodiments of the present disclosure. Apparently, the described embodiments are merely a part rather than all of the embodiments of the present disclosure. All other embodiments obtained by those of ordinary skill in the art based on the embodiments of the present disclosure without creative efforts should fall within the protection scope of the present disclosure.

In this embodiment, in an application scenario targeting simultaneous imaging of four nuclides, namely $^{1}$H, $^{19}$F, $^{23}$Na, and $^{31}$P, in a rabbit leg, $^{19}$F serves as an exogenous perfluorooctylbromide (PFOB) molecular imaging probe, and $^{1}$H has a planar resolution of 1 millimeter (mm).

Figure 2:
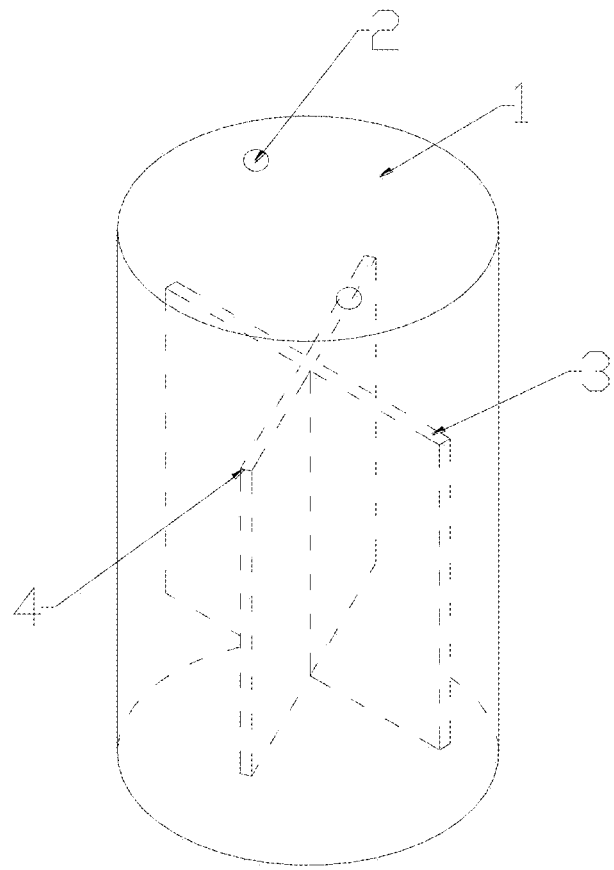
FIG. 2 is a three-dimensional diagram of a sealed container.
Figure 3:
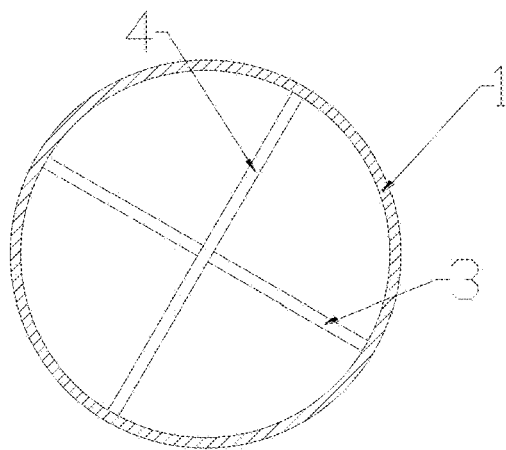
FIG. 3 is a sectional view of the sealed container.

As shown in FIGS. 1 to 3, a phantom for multinuclear simultaneous integrated magnetic resonance imaging (MRI), specifically, a phantom for four-nuclear ($^{1}$H/$^{19}$F/$^{23}$Na/$^{31}$P) simultaneous imaging for a rabbit leg includes four sealed containers 1. The four sealed containers 1 are all provided with cylindrical shells. An upper end of each of the sealed containers 1 is provided with two water inlets 2. The water inlets 2 are threaded holes sealed with a screw and a sealing O-ring.

As shown in FIGS. 2 and 3, a set of the partition I 3 and partition II 4 are provided in the sealed container 1 and are interlocked to form a cross-shaped assembly. A height of the cross-shaped assembly is shorter than an inner height of the sealed container 1. A height center of the cross-shaped assembly coincides with a height center of the sealed container 1. That is, an upper end and a lower end of the cross-shaped assembly are spaced apart from the sealed container 1. The cross-shaped assembly divides the sealed container 1 into a plurality of subspaces, wherein the plurality of subspaces are interconnected. Thicknesses of the partition I 3 and the partition II 4 depend on a ratio of gyromagnetic ratios of non-proton nuclide (X) and proton nuclide ($^{1}$H) in the imaging nuclide. The thickness of the partition I 3 is equal to a resolution of $^{1}$H, and the thickness of the partition II 4 is equal to $\gamma_H/\gamma_X$ times the resolution of $^{1}$H. $\gamma_X$ corresponds to the gyromagnetic ratios of $^{19}$F, $^{23}$Na, $^{31}$P, and $^{1}$H, respectively, and $\gamma_H$ is the gyromagnetic ratio of $^{1}$H. The sealed containers 1, the screw, the partition I 3, and the partition II 4 are made of non-magnetic polytetrafluoroethylene, and the sealing O-ring is a corrosion-resistant rubber ring.

Figure 4:
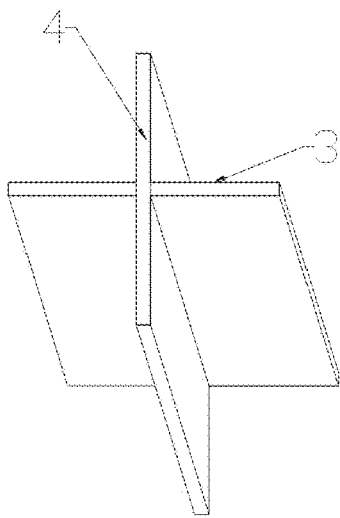
FIG. 4 shows a cross-shaped assembly corresponding to a gyromagnetic ratio of a nuclide $^{19}$F.

As shown in FIG. 4, in a cross-shaped assembly corresponding to the gyromagnetic ratio of $^{19}$F, the thicknesses of the partition I 3 and the partition II 4 depend on a ratio of the gyromagnetic ratios of $^{1}$H and $^{19}$F, which is 1.06. The thickness of the partition I 3 is 1 mm, and the thickness of the partition II 4 is 1.06 mm.

Figure 5:
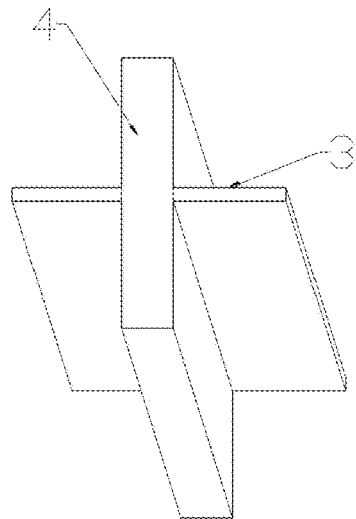
FIG. 5 shows a cross-shaped assembly corresponding to a gyromagnetic ratio of a nuclide $^{23}$Na.

As shown in FIG. 5, in a cross-shaped assembly corresponding to the gyromagnetic ratio of $^{23}$Na, the thicknesses of the partition I 3 and the partition II 4 depend on a ratio of the gyromagnetic ratios of $^{1}$H and $^{23}$Na, which is 3.78. The thickness of the partition I 3 is 1 mm, and the thickness of the partition II 4 is 3.78 mm.

Figure 6:
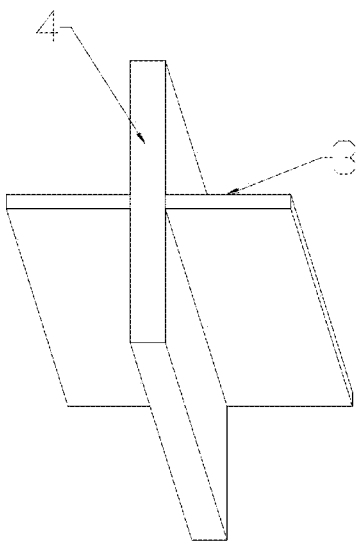
FIG. 6 shows a cross-shaped assembly corresponding to a gyromagnetic ratio of a nuclide $^{31}$P.

As shown in FIG. 6, in a cross-shaped assembly corresponding to the gyromagnetic ratio of $^{31}$P, the thicknesses of the partition I 3 and the partition II 4 depend on a ratio of the gyromagnetic ratios of $^{1}$H and $^{31}$P, which is 2.47. The thickness of the partition I 3 is 1 mm, and the thickness of the partition II 4 is 2.47 mm.

Figure 7:
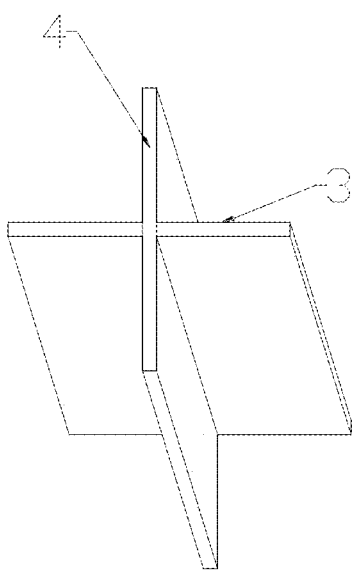
FIG. 7 shows a cross-shaped assembly corresponding to a gyromagnetic ratio of a nuclide $^{1}$H.

As shown in FIG. 7, in a cross-shaped assembly corresponding to the gyromagnetic ratio of $^{1}$H, the thickness of the partition I 3 is 1 mm, and the thickness of the partition II 4 is also 1 mm.

The sealed container 1 is filled with a mixture. The mixture is a mixed solution including all pre-imaging nuclides or a homogeneous dispersion system of a semi-solid like gel. For example, the mixture is prepared as follows. Analytically pure sodium dihydrogen phosphate (NaH$_2$PO$_4$) is dissolved in water (water provides $^1$H), and agarose is added. 80° C. water-bath heating and evenly stirring are conducted. An appropriate amount of a PFOB molecular imaging probe is added, with a concentration greater than a concentration of an exogenous PFOB molecular imaging probe injected into the rabbit leg. For example, a concentration ratio of 1.2 (with an excess of 20%) is adopted. After evenly stirring is conducted, cooling is conducted. The PFOB molecular imaging probe is evenly dispersed in the agarose gel system. Agarose content is controlled around 4 g/L. Concentrations of $^{23}$Na and $^{31}$P are controlled around 100 mmol/L. A resonant frequency of $^{31}$P in sodium dihydrogen phosphate of the mixture is consistent with that of inorganic phosphorus (Pi) in the living organism, and it has a single peak. The resonant frequency of $^{23}$Na in sodium dihydrogen phosphate is consistent with that of a sodium salt in the living organism, and it has a single peak. The PFOB molecular imaging probe in the mixture is consistent with the PFOB molecular imaging probe injected into a tumor region of the rabbit leg, with the same resonant frequency for selective excitation of the same spectral peak.

An application method of the phantom for multinuclear simultaneous integrated MRI is as follows.

Before a multinuclear MRI scan starts, the four sealed containers 1 are placed in a coplanar and non-collinear manner around pre-imaging part 5 (as shown in FIG. 1). A selected imaging slice includes central regions of the sealed containers 1. An image presented by the phantom imaging includes a cross-shaped structure. For the imaging of the rabbit hind leg, the four sealed containers 1 circle around the rabbit leg and are secured with an elastic strap. The imaging slice includes the central regions of the four sealed containers 1, and the image presented by the phantom includes a cross-shaped structure.

The above described are merely preferred embodiments of the present disclosure, and not intended to limit the present disclosure. Any modifications, equivalent replacements and improvements made within the spirit and principle of the present disclosure should all fall within the scope of protection of the present disclosure.

What is claimed is:

1. A phantom for multinuclear simultaneous integrated magnetic resonance imaging (MRI), comprising a plurality of sealed containers, wherein a first partition and a second partition are provided in each of the plurality of sealed containers and intersect with each other; the first partition and the second partition divide each of the plurality of sealed containers into a plurality of subspaces, wherein the plurality of subspaces are interconnected; a thickness of the first partition is equal to a resolution of a nuclide $^1$H, and a thickness of the second partition is $\gamma_H/\gamma_X$ times of the resolution of the nuclide $^1$H, wherein $\gamma_H$ is a gyromagnetic ratio of the nuclide $^1$H, and $\gamma_X$ is a gyromagnetic ratio of a pre-imaging nuclide X; each of the plurality of sealed containers is filled with a mixture; and the mixture comprises all pre-imaging nuclides including the nuclide $^1$H and the pre-imaging nuclide X.

2. The phantom for multinuclear simultaneous integrated MRI according to claim 1, wherein there are a total of n pre-imaging nuclides; n is an integer, n≥2, and one of the nuclides is $^1$H; when n=2, a remaining nuclide is a non-proton nuclide $X_1$, wherein $\gamma_{X\_1}$ is the gyromagnetic ratio of a pre-imaging nuclide $X_1$; and when n≥3, remaining nuclides are non-proton nuclides $X_1, X_2, \ldots$, and $X_{n-1}$, wherein $\gamma_{X\_1}, \gamma_{X\_2} \ldots$ and $\gamma_{Xn-1}$ is the gyromagnetic ratio of a pre-imaging nuclides $X_1, X_2, \ldots$, and $X_{n-1}$, respectively.

3. The phantom for multinuclear simultaneous integrated MRI according to claim 2, wherein when n=2; there are three sealed containers in total; and the gyromagnetic ratios of the nuclides in the three sealed containers are gyromagnetic ratios of $^1$H, and $X_1$.

4. The phantom for multinuclear simultaneous integrated MRI according to claim 3, wherein each nuclide in the mixture has a concentration greater than a concentration of the corresponding nuclide in the living organism.

5. The phantom for multinuclear simultaneous integrated MRI according to claim 2, wherein when n≥3, there are n sealed containers in total; and the gyromagnetic ratios of the nuclides in the n sealed containers are gyromagnetic ratios of $^1$H, $X_1, X_2, \ldots$, and $X_{n-1}$.

6. The phantom for multinuclear simultaneous integrated MRI according to claim 5, wherein each nuclide in the mixture has a concentration greater than a concentration of the corresponding nuclide in the living organism.

7. The phantom for multinuclear simultaneous integrated MRI according to claim 2, wherein each nuclide in the mixture has a concentration greater than a concentration of the corresponding nuclide in the living organism.

8. The phantom for multinuclear simultaneous integrated MRI according to claim 1, wherein a resonant frequency of the pre-imaging nuclide in the mixture is consistent with an excitation frequency of the pre-imaging nuclide in a living organism.

9. The phantom for multinuclear simultaneous integrated MRI according to claim 8, wherein each nuclide in the mixture has a concentration greater than a concentration of the corresponding nuclide in the living organism.

10. The phantom for multinuclear simultaneous integrated MRI according to claim 1, wherein an MR peak of the pre-imaging nuclide in the mixture is a single peak; and alternatively, a compound where the nuclide is located belongs to a same substance as an exogenous compound injected into a living organism.

11. The phantom for multinuclear simultaneous integrated MRI according to claim 10, wherein each nuclide in the mixture has a concentration greater than a concentration of the corresponding nuclide in the living organism.

12. The phantom for multinuclear simultaneous integrated MRI according to claim 1, wherein each nuclide in the mixture has a concentration greater than a concentration of the corresponding nuclide in the living organism.

13. The phantom for multinuclear simultaneous integrated MRI according to claim 1, wherein each of the plurality of sealed containers is provided with a cylindrical shell; the first partition and the second partition intersect to form a cross-shaped assembly; and an upper end and a lower end of the cross-shaped assembly are spaced apart from each of the plurality of sealed containers.

14. An application method of the phantom for multinuclear simultaneous integrated MRI according to claim 1, comprising: placing the plurality of sealed containers in a coplanar and non-collinear manner around a pre-imaging part, ensuring that a selected imaging slice comprises central regions of the plurality of sealed containers and the first partition and the second partition are present.

15. The application method according to claim 14, wherein the plurality of sealed containers are placed at equal distances around the pre-imaging part and secured with an elastic strap.

16. The application method according to claim 14, wherein in the phantom for multinuclear simultaneous integrated MRI, there are a total of n pre-imaging nuclides; n is an integer, n≥2, and one of the nuclides is $^1$H; when n=2, a remaining nuclide is a non-proton nuclide $X_1$, wherein $\gamma_{X\_1}$ is the gyromagnetic ratio of a pre-imaging nuclide $X_1$; and when n≥3, remaining nuclides are non-proton nuclides $X_1$, $X_2$, ..., and $X_{n-1}$ wherein $\gamma_{X\_1}$, $\gamma_{X\_2}$ ... and $\gamma_{Xn-1}$ is the gyromagnetic ratio of a pre-imaging nuclides $X_1$, $X_2$, ..., and $X_{n-1}$, respectively.

17. The application method according to claim 16, wherein when n=2; there are three sealed containers in total; and the gyromagnetic ratios of the nuclides in the three sealed containers are $\gamma_X$ gyromagnetic ratios of $^1$H, and $X_1$.

18. The application method according to claim 16, wherein when n≥3, there are n sealed containers in total; and the gyromagnetic ratios of the nuclides in the n sealed containers $\gamma_X$ are gyromagnetic ratios of $^1$H, $X_1$, $X_2$, ..., and $X_{n-1}$.

19. The application method according to claim 14, wherein in the phantom for multinuclear simultaneous integrated MRI, a resonant frequency of the pre-imaging nuclide in the mixture is consistent with an excitation frequency of the pre-imaging nuclide in a living organism.

20. The application method according to claim 14, wherein in the phantom for multinuclear simultaneous integrated MRI, an MR peak of the pre-imaging nuclide in the mixture is a single peak; and alternatively, a compound where the nuclide is located belongs to a same substance as an exogenous compound injected into a living organism.

* * * * *